June 28, 1966 H. W. KERRIGAN Plant Pat. 2,647
AZALEA PLANT
Filed Oct. 26, 1964
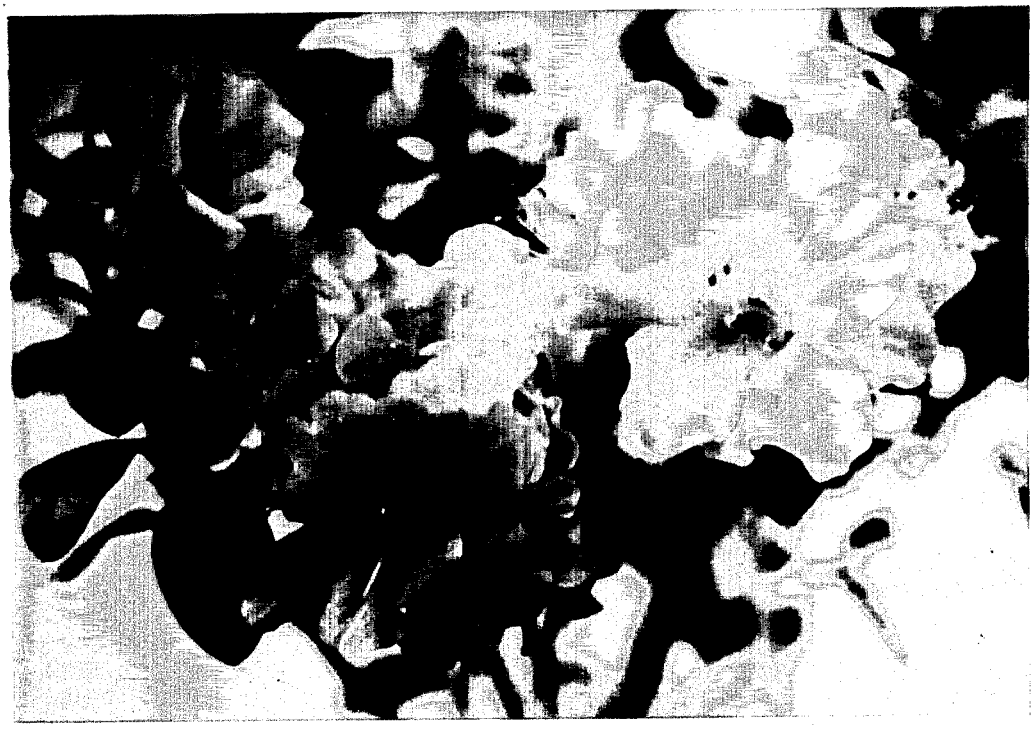
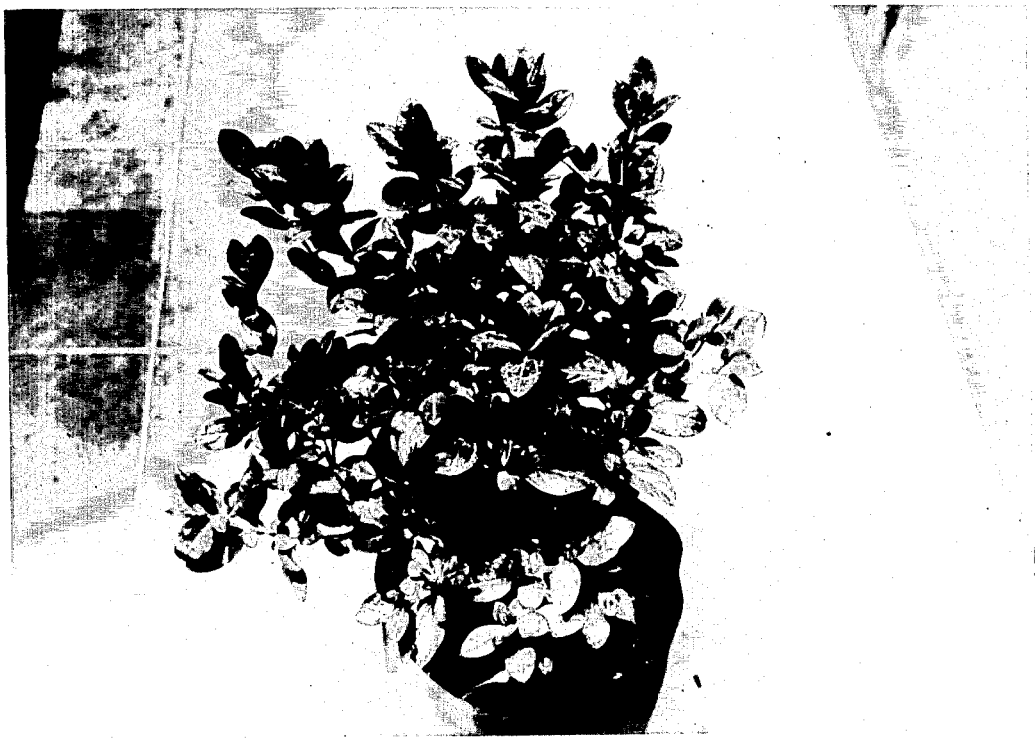

United States Patent Office

Plant Pat. 2,647
Patented June 28, 1966

2,647
AZALEA PLANT

Howard W. Kerrigan, 300 Totterdale, Oakland, Calif.

Filed Oct. 26, 1964, Ser. No. 406,642
1 Claim. (Cl. Plt.—57)

The invention relates to a new and distinct variety of evergreen azalea suitable for both garden and forcing use, intermediate between the Kurume and Belgian Indica types, primarily characterized by a combination of color, which is rich, glowing blood red and by the superior substance and sheen of the flower coupled with vigorous growth and exceptionally abundant dark green glossy foliage.

The variety is intermediate in flower size and typical of the Sander's hybrids, particularly the variety "Hexe," though the growth is more upright and the foliage larger than most azaleas of this type. My new variety is a seedling of the cross "Crimson Glory" × "Vivid," a Sander's hybrid. The breeding program leading to the development of my new variety was initiated in 1948.

The main objective of this program was to produce an evergreen garden azalea with an improved richer red color than "Hexe" and with stronger and more rapid growth and a variety which would bud heavily and respond satisfactorily to early forcing. My new variety of azalea plant is illustrated in the two photographs accompanying and forming a part of this specification. (1 sheet).

My new variety of azalea was first propagated by cuttings in 1952 in Oakland, California, and has come true to form through successive generations of asexually produced plants.

A comparison of my new variety to other azaleas of the Sander's hybrid type indicates that it is unique and significantly superior to other forms. When compared to the pollen parent "Vivid," the flower is larger, richer red with better substance and better growth habit and foliage. When compared to the seed parent "Crimson Glory," it has better color, better foliage and more rapid growth. It has a vastly superior color to "Hexe," the most widely grown of all the Sander's hybrids, and grows at a rate 1½ to 2 times at great.

In the following description of my new variety, the color designations are those employed in the Horticultural Color Chart issued by Wilson Color Ltd., in collaboration with the Royal Horticultural Society.

*Description.*—Evergreen shrub to three feet, upright from the base, spreading and flat topped at maturity. The stems slender, stiff, and erect, reddish brown when older. The oldest stems grey. Young stems moderately pubescent. The pubescence white to tan, scaly, scarious, narrowly lanceolate, flattened, evenly attenuated margins usually entire, sometimes dissected with the secondary lobes giving a conspicuously fimbriate appearance to the individual hairs. The foliage short petiolate dark green (0960) nitid above, light green (0960/3), shiny to dull below; pubescent, the pubescent sparse, scattered, inconspicuous, extremely fine, hyaline, white to light tan, heavier on the prominent midrib below. The leaf margin inconspicuously finely ciliate, entire, glandular nucronate.

The petiole ¼ inch long to somewhat shorter in small leaves, the blade of essentially two size classes, the lower leaves small ovate with blades about ¾ inch long and 7/16 inch wide often obovate, the distal blades larger 1½ inches long, 11/16 inch wide, often obovate. The bud of the inflorescence 7/16 inch long, 5/16 inch wide, tan, pubescent; the pubescence reddish brown to tan moderately dense, wooly. The flowers short pedicilate, hose-in-hose. The pedicel ⅜ inch long by 3/32 inch wide slightly flaring at the receptacle; pubescent, the pubescence strigose moderately dense light tan, sub-hyaline, acute. The calyx is corolliform, cherry red (722/2) broadly flaring, perfect, five lobed, inconspicuously irregular, ventral lobe 1 inch long and ¾ inch wide, lateral lobes ⅞ inch long and 9/14 inch wide, the two dorsal lobes unequal, 9/16 x 7/16 to ⅞ x ⅝ inch. The lobes are broadly linear-ovate, auriculate. The margins of the lobes sub-crenulate, ciliate. The tube of the calyx is ⅜ inch across at the throat and ⅜ inch deep. The dorsal two lobes are inconspicuously marked Chrysanthemum Crimson (824/2) on their proximal ¼. The corolla is Cherry Red (722/2) irregular 1⅜ inch deep by 1¾ inch across. The tube is ⅝ inch deep, flaring, ⅛ inch at the base, ⅝ inch at the throat, slightly fluted, five lobed. The limbs of the corolla are polymorphic. The lateral lobes are asymmetrical ⅞ inch x ¾ inch. The 2 ventral lobes are dimorphic, one ⅞ inch x ⅞ inch, the other ⅞ inch x ¾ inch. The margins of the lobes are entire, slightly undulate. The base of the dorsal lobe and the upper proximal portion of the lateral lobes are marked Chrysanthemum Crimson (824/2) with the markings descending into the distal portion of the dorsal surface of the mouth of the tube. The stamens are 5–7 straight to slightly curved distally, 1–1⅜ inches long, the filament slender Cherry Red (772/3), white at the base. Sometimes, accrescent and petaloidal. Anthers Chrysanthemum Crimson (824/2), 1/16 inch long and 1/32 inch wide. The pistil 1⅝ inches long. The stigma capitate, small, 1/32 inch across, Chrysanthemum Crimson (824/1). The style slender, Cherry Red (722/2) curved distally upward, slightly flared below the stigma, pubescent proximally. The pubescence long, slender, silky, hyaline, lanceolate with sparsely fimbriated margins in some cases. The ovary narrowly urseolate, truncate, green below, reddish above, densely pubescent; the pubescence long, silky, hyaline and exceeding the ovary by 1/32 inch.

Having thus disclosed my invention, I claim:

A new and distinct variety of azalea plant as described and shown characterized particularly as to novelty by the unique combination of an evergreen habit, vigorous growth and exceptionally abundant dark green glossy foliage, large flower size, short pedicellate hose-in-hose flower form having superior substance and sheen, rich glowing blood red color of the flowers, and a suitability for garden and greenhouse forcing, intermediate between the Kurume and Belgian Indica types.

No references cited.

ABRAHAM G. STONE, *Primary Examiner.*

R. E. BAGWILL, *Assistant Examiner.*